(12) United States Patent
Jung et al.

(10) Patent No.: US 10,434,336 B2
(45) Date of Patent: Oct. 8, 2019

(54) ION THERAPY DEVICE AND THERAPY METHOD USING ION BEAM

(71) Applicant: ELECTRONICS AND TELECOMMUNICATIONS RESEARCH INSTITUTE, Daejeon (KR)

(72) Inventors: Moon Youn Jung, Daejeon (KR); SooYeul Lee, Daejeon (KR); Jang Hwan Choi, Daejeon (KR); Jinsun Kim, Daejeon (KR)

(73) Assignee: ELECTRONICS & TELECOMMUNICATIONS RESEARCH INSTITUTE, Daejeon (KR)

( * ) Notice: Subject to any disclaimer, the term of this patent is extended or adjusted under 35 U.S.C. 154(b) by 58 days.

(21) Appl. No.: 15/711,925

(22) Filed: Sep. 21, 2017

(65) Prior Publication Data
US 2018/0078791 A1 Mar. 22, 2018

(30) Foreign Application Priority Data

Sep. 21, 2016 (KR) .................. 10-2016-0121010
Feb. 8, 2017 (KR) .................. 10-2017-0017744

(51) Int. Cl.
*A61N 5/10* (2006.01)
*A61B 6/00* (2006.01)
(Continued)

(52) U.S. Cl.
CPC .......... *A61N 5/1049* (2013.01); *A61B 6/032* (2013.01); *A61B 6/12* (2013.01); *A61B 6/469* (2013.01);
(Continued)

(58) Field of Classification Search
CPC .......... A61B 6/032; A61B 6/12; A61B 6/469; A61B 6/484; A61N 5/1048; A61N 5/1071;
(Continued)

(56) References Cited

U.S. PATENT DOCUMENTS 7,212,608 B2 * 5/2007 Nagamine ............... A61B 6/04
378/205
2006/0163495 A1 7/2006 Hiramoto et al.
(Continued)

FOREIGN PATENT DOCUMENTS

| JP | 2006-239403 A | 9/2006 |
| JP | 2016-144573 A | 8/2016 |
| KR | 10-0695377 B1 | 3/2007 |

OTHER PUBLICATIONS

Bong Hwan Hong et al., "Visualization experiment of 30 MeV proton beam irradiated water target", Nuclear Instrument and Methods in Physics Research A, 2011, pp. 103-107, vol. 655, Elsevier B.V.
(Continued)

*Primary Examiner* — Wyatt A Stoffa (57) ABSTRACT

Provided is a therapy method using an ion beam, including injecting the ion beam to a target spot in a body of an examinee, measuring a Bragg peak spot of the ion beam injected into the body of the examinee, and adjusting the target spot using the measured Bragg peak spot, wherein the measuring of the Bragg peak spot comprises measuring a spot of a microbubble generated inside the body of the examinee.

17 Claims, 6 Drawing Sheets

(51) Int. Cl.
*G01T 1/29* (2006.01)
*A61B 6/03* (2006.01)
*A61B 6/12* (2006.01)

(52) U.S. Cl.
CPC ............ *A61B 6/484* (2013.01); *A61N 5/1084* (2013.01); *G01T 1/29* (2013.01); *G01T 1/2985* (2013.01); *A61N 5/1065* (2013.01); *A61N 5/1069* (2013.01); *A61N 2005/1051* (2013.01); *A61N 2005/1061* (2013.01); *A61N 2005/1062* (2013.01); *A61N 2005/1087* (2013.01); *A61N 2005/1098* (2013.01)

(58) Field of Classification Search
CPC ...... A61N 5/10; A61N 5/1049; A61N 5/1065; A61N 5/109; A61N 2005/1061; A61N 2005/1087; G01T 1/29; G01T 1/2985
See application file for complete search history.

(56) References Cited

U.S. PATENT DOCUMENTS

| | | | |
|---|---|---|---|
| 2011/0006224 A1* | 1/2011 | Maltz | A61B 6/4233 250/492.3 |
| 2013/0034208 A1* | 2/2013 | Heid | A61N 5/1049 378/62 |
| 2013/0110994 A1 | 5/2013 | Kang et al. | |
| 2013/0289331 A1 | 10/2013 | Jung et al. | |
| 2014/0066755 A1* | 3/2014 | Matteo | A61B 6/032 600/427 |

OTHER PUBLICATIONS

Bong Hwan Hong et al., "Self-overcoming of the boiling condition by pressure increment in a water target irradiated by proton beam", Nuclear Instrument and Methods in Physics Research A, 2013, pp. 6-10, vol. 728, Elsevier B.V.

* cited by examiner

FIG. 6

ION THERAPY DEVICE AND THERAPY METHOD USING ION BEAM

CROSS-REFERENCE TO RELATED APPLICATIONS

This U.S. non-provisional patent application claims priority under 35 U.S.C. § 119 of Korean Patent Application Nos. 10-2016-0121010, filed on Sep. 21, 2016, and 10-2017-0017744, filed on Feb. 8, 2017, the entire contents of which are hereby incorporated by reference.

BACKGROUND

The present disclosure herein relates to an ion therapy device using an ion beam and a therapy method for removing a tumor using the same.

There are X-ray therapy, electron beam therapy, and ion beam therapy in radiation therapies. It is cheap enough to implement using a simple device, and thus the X-ray therapy is universally used among the radiation therapies. In 1950s, it was proved that a tumor might be treated when an electron was accelerated by an accelerator to be injected to a tumor, but the electron beam therapy actually became one of radiation therapies as the electron accelerator was miniaturized in 1980s. On the other hand, the X-ray therapy or electron beam therapy destructs DNA of a cancer cell by cutting a hydrogen bond in the cancer cell, but accompanies a side effect that healthy cells existing on a travel path of the ray or beam are also seriously damaged. As a method for reducing such a problem that a normal cell is exposed to radiation, techniques such as an intensity-modulated radiation therapy (IMRT), tomo therapy, and cyber knife have been developed, but these techniques do not perfectly solve the above described side effects.

The ion-beam therapy draws attention as a therapy means capable of reducing a side effect of the X-ray therapy or electron beam therapy. Similarly to the electron beam, the ion beam should be also accelerated to have a rapid speed so that the ion beam penetrates through a material. Even though the ion beam is gradually decelerated during penetration through a certain material, the ion beam experiences the highest energy loss of ionizing radiation right before stop. Such a phenomenon is called as 'Bragg peak' by taking its name from William Henry Bragg who discovered the same in 1903. For the ion beam therapy, when speeds of ions are accurately controlled, malignant tumors may be selectively and locally treated. When a tumor is located deep in a body, a proton or ion having very high energy should be accelerated outside the body.

The Bragg peak of an ion beam incident to body tissues may be differently formed for each patient, even when the ion beam has the same kinetic energy. That is because an error may occur due to different cell components for each organ structure inside the body and for each individual, and an initial condition such as an incidence direction may not be accurate due to an error in position information. Accordingly, it is urgent to develop a technique capable of checking the Bragg peak in real time, while injecting an ion beam into a human body.

SUMMARY

The present disclosure provides an ion therapy device and a therapy method capable of removing a tumor inside the body of an examinee and examining a spot at which a Bragg peak is formed inside the body of the examinee.

Issues to be addressed in the present disclosure are not limited to those described above and other issues unmentioned above will be clearly understood by those skilled in the art from the following description.

An embodiment of the inventive concept provides a therapy method using an ion beam, including: injecting the ion beam to a target spot in a body of an examinee; measuring a Bragg peak spot of the ion beam injected into the body of the examinee; and adjusting the target spot using the measured Bragg peak spot, wherein the measuring of the Bragg peak spot comprises measuring a spot of a microbubble generated inside the body of the examinee.

In an embodiment, the injecting of the ion beam and the measuring of the Bragg peak spot may be performed substantially at a same time.

In an embodiment, the adjusting of the target spot may include adjusting at least one of an injection direction and injection intensity of the ion beam on a basis of the measured Bragg peak spot.

In an embodiment, the measuring of the Bragg peak spot may include: injecting an X-ray into the body of the examinee; acquiring, from the X-ray, an X-ray image of the body of the examinee; and measuring, from the X-ray image, the spot of the microbubble generated in the ion beam.

In an embodiment, the X-ray image may be at least one of an X-ray phase contrast image, X-ray subtraction image, X-ray phase contrast subtraction image, and X-ray tomography image.

In an embodiment, the ion beam and X-ray may be injected to the target spot inside the body of the examinee, and the injection direction of the ion beam toward the body of the examinee and the injection direction of the X-ray toward the body of the examinee may not overlap each other.

In an embodiment, the injections of the ion beam and the X-ray may be performed during revolution around the body of the examinee.

In an embodiment, a diameter of the microbubble may be several hundreds Å to several hundreds μm.

In an embodiment of the inventive concept, a therapy method using an ion beam, including: injecting the ion beam into a body of an examinee; injecting an X-ray into the body of the examinee to which the ion beam is injected; acquiring, from the X-ray, an X-ray image of the body of the examinee; and measuring, from the X-ray image, a spot of a microbubble generated in the ion beam to check a Bragg peak spot of the ion beam.

In an embodiment, a diameter of the microbubble may be several hundreds Å to several hundreds μm.

In an embodiment, the X-ray image may be at least one of an X-ray phase contrast image, X-ray subtraction image, X-ray phase contrast subtraction image, and X-ray tomography image.

In an embodiment, the ion beam and X-ray may be injected to a target spot inside the body of the examinee, and an injection direction of the ion beam toward the body of the examinee and an injection direction of the X-ray toward the body of the examinee may not overlap each other.

In an embodiment, the ion beam and X-ray may be injected to a target spot inside the body of the examinee, the therapy method may further include adjusting the target spot using the Bragg peak spot, wherein the adjusting of the target spot comprises adjusting at least one of an injection direction and injection intensity of the ion beam on a basis of the measured Bragg peak spot.

In an embodiment of the inventive concept, an ion therapy device includes: an ion beam generating unit configured to generate an ion beam; an ion beam injecting unit configured to inject the ion beam to a body of an examinee; a gantry disposed to enclose the body of the examinee and configured to revolve around the body of the examinee; and an X-ray imaging device configured to measure a spot of a microbubble inside the body of the examinee.

In an embodiment, the X-ray imaging device may be at least one of an X-ray phase contrast imaging device, X-ray subtraction imaging device, X-ray phase contrast subtraction imaging device, and X-ray tomography imaging device.

In an embodiment, the ion beam injecting unit may be combined to one side of the gantry.

Specifics of other embodiments are incorporated in the following description and the attached drawings.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Advantages and features of the present invention, and methods for achieving the same will be cleared with reference to exemplary embodiments described later in detail together with the accompanying drawings. However, the present invention is not limited to the following exemplary embodiments, but realized in various forms. In other words, the present exemplary embodiments are provided just to complete disclosure the present invention and make a person having an ordinary skill in the art understand the scope of the invention. The present invention should be defined by only the scope of the accompanying claims. Throughout this specification, like numerals refer to like elements.

The terms and words used in the following description and claims are to describe embodiments but are not limited the inventive concept. As used herein, the singular forms "a," "an" and "the" are intended to include the plural forms as well, unless the context clearly indicates otherwise. It will be further understood that the terms "comprises" and/or "comprising" used herein specify the presence of stated components, operations and/or elements but do not preclude the presence or addition of one or more other components, operations and/or elements.

Example embodiments are described herein with reference to cross-sectional views and/or plan views that are schematic illustrations of example embodiments. In the drawings, the thicknesses of layers and regions are exaggerated for clarity. As such, variations from the shapes of the illustrations as a result, for example, of manufacturing techniques and/or tolerances, are to be expected. Thus, example embodiments should not be construed as limited to the particular shapes of regions illustrated herein but may be to include deviations in shapes that result, for example, from manufacturing. Thus, the regions illustrated in the figures are schematic in nature and their shapes may be not intended to illustrate the actual shape of a region of a device and are not intended to limit the scope of example embodiments.

Figure 1:
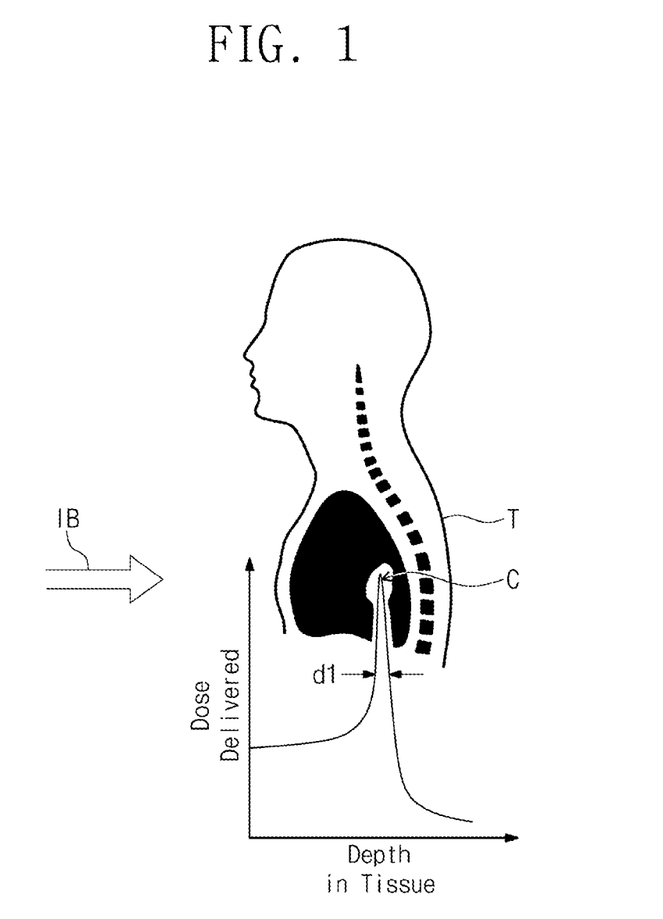
FIG. 1 shows removing of a tumor inside the body of an examinee using an ion beam.

FIG. 1 shows removing of a tumor inside the body of an examinee T using an ion beam. An ion beam IB may be injected to a tumor portion C including tumor cells inside the body of the examinee T. The ion beam IB may be carbon ions or cations. The ion beam IB collided with the tumor region C may generate reactive oxygen to disturb tumor cells in the tumor region C, and then may hinder the tumor cells from being grown or necrotize the tumor cells. In addition, that the ion beam IB disturbs the tumor cells in the tumor portion C may be that the ion beam IB disturbs the dual-spiral DNA of the tumor cell or a metabolic process inside the nucleus of the tumor cell. The ion beam IB may set and injected at a spot of the tumor portion C obtained by an image diagnosis device such as a magnetic resonance imaging (MM) device, a computer tomography (CT), a positron emission tomography (PET), or an ultrasonic wave device. Accordingly, the ion beam IB may be incident with specific energy in a specific direction in order to form a Bragg peak, when reaching the tumor portion C. At this point, it is important to form the Bragg peak at an intended spot, namely, the tumor portion C. The full width at half maximum d1 may be formed at the spot where the Bragg peak is formed.

Figure 2:
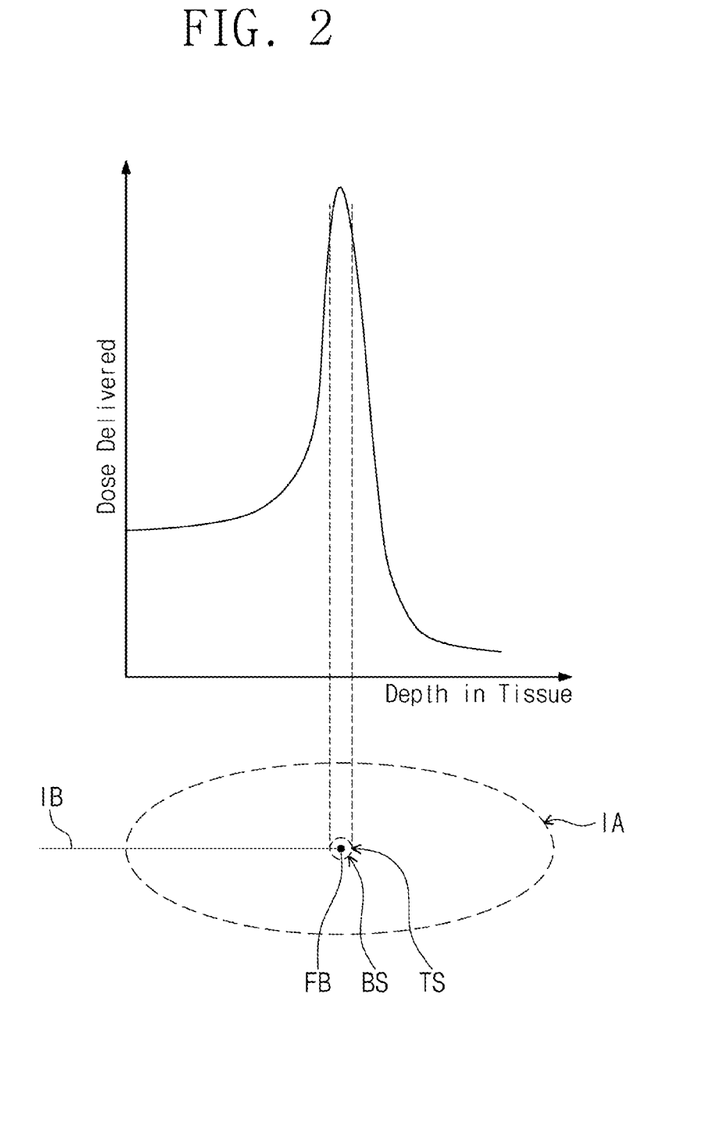
FIG. 2 shows forming of a microbubble at a Bragg peak spot at which an ion beam forms a Bragg peak.

FIG. 2 shows that a microbubble FB is formed at a Bragg peak spot BS at which the ion beam IB forms the Bragg peak. Referring to FIG. 2, the microbubble FB may be formed in the ion beam IB. The microbubble FB may be formed at the Bragg peak spot BS where the Bragg peak is formed among an ion beam distributable region 1A in which the ion beam IB being injected to a target spot TS inside the body of the examinee may be distributed. The diameter of the microbubble FB may be several hundreds Å to several hundreds μm. For example, the diameter of the microbubble FB may be about 100 Å to about 200 μm. As shown in FIG. 2, the Bragg peak spot BS and the target spot TS may be coincident with each other.

Figure 3:
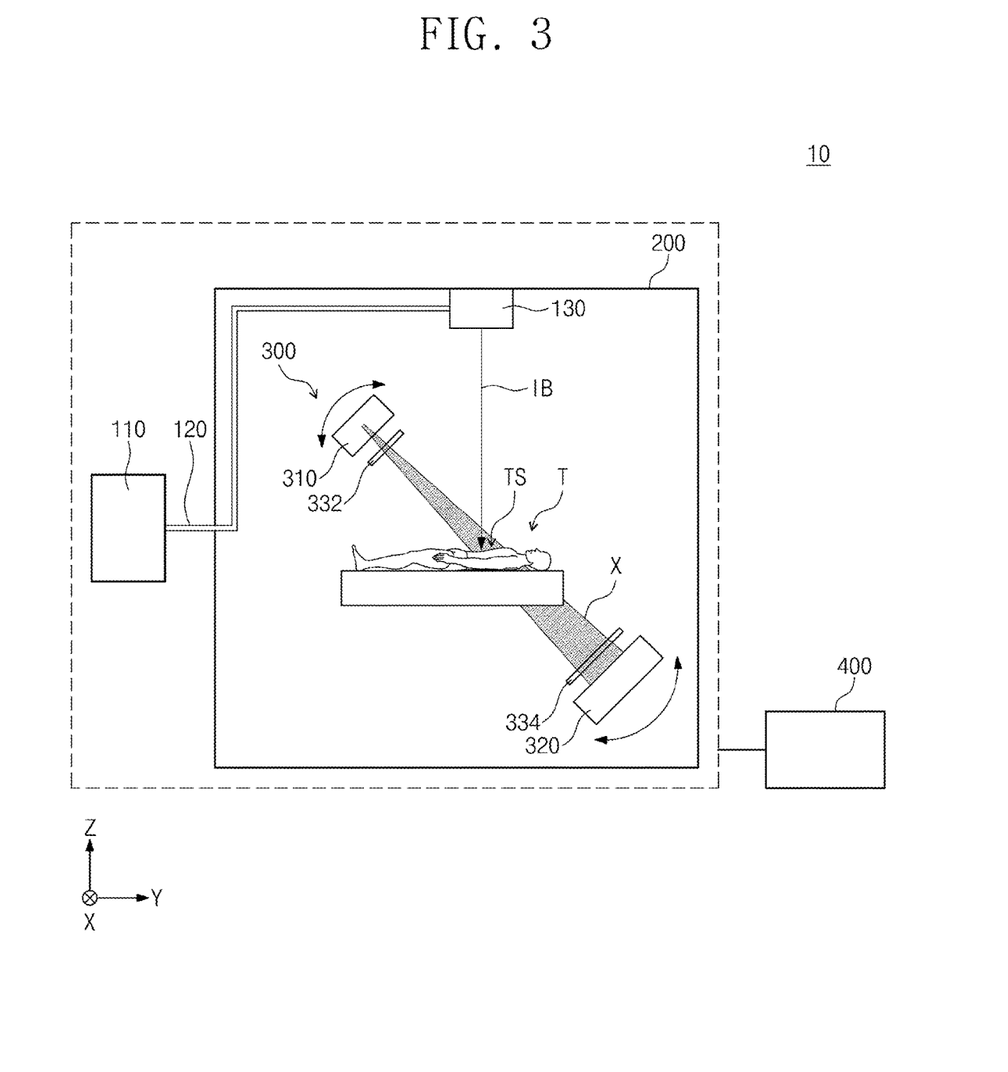
FIG. 3 schematically shows an ion therapy device according to an embodiment of the inventive concept.
Figure 4:
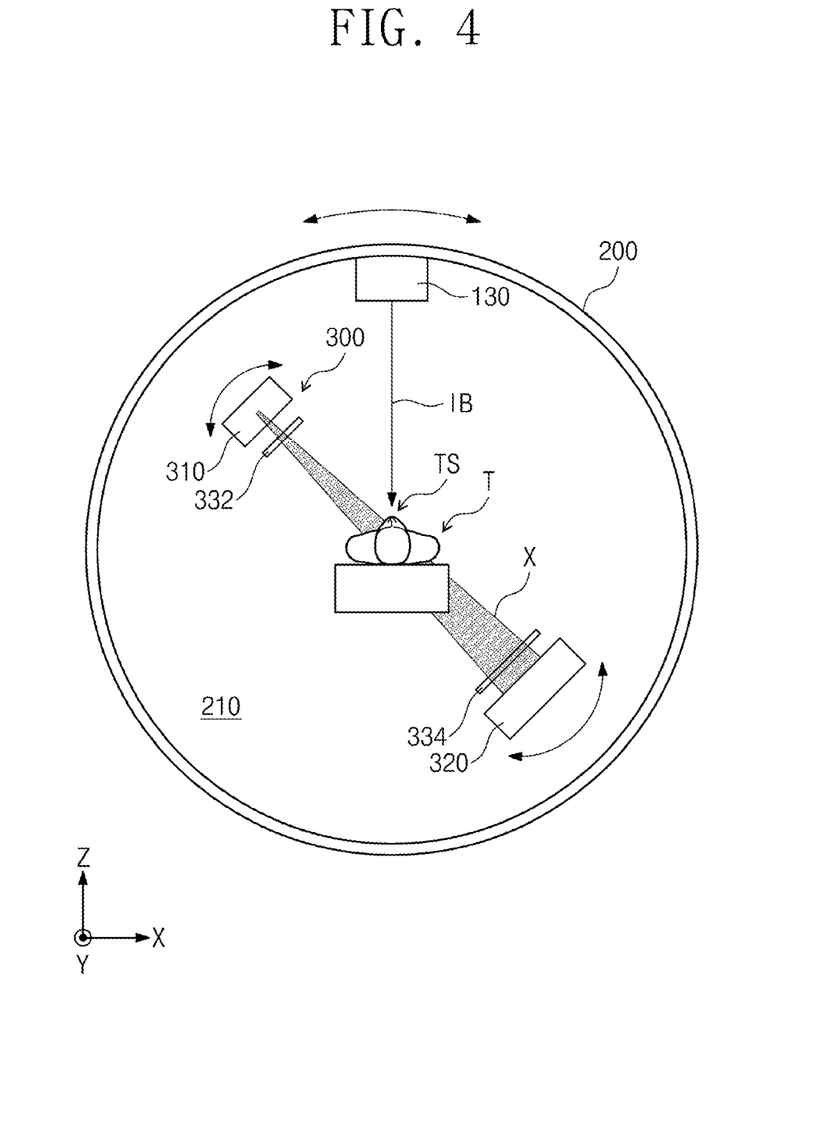
FIG. 4 is a drawing of a gantry of FIG. 3 viewed from a front.
Figure 5:
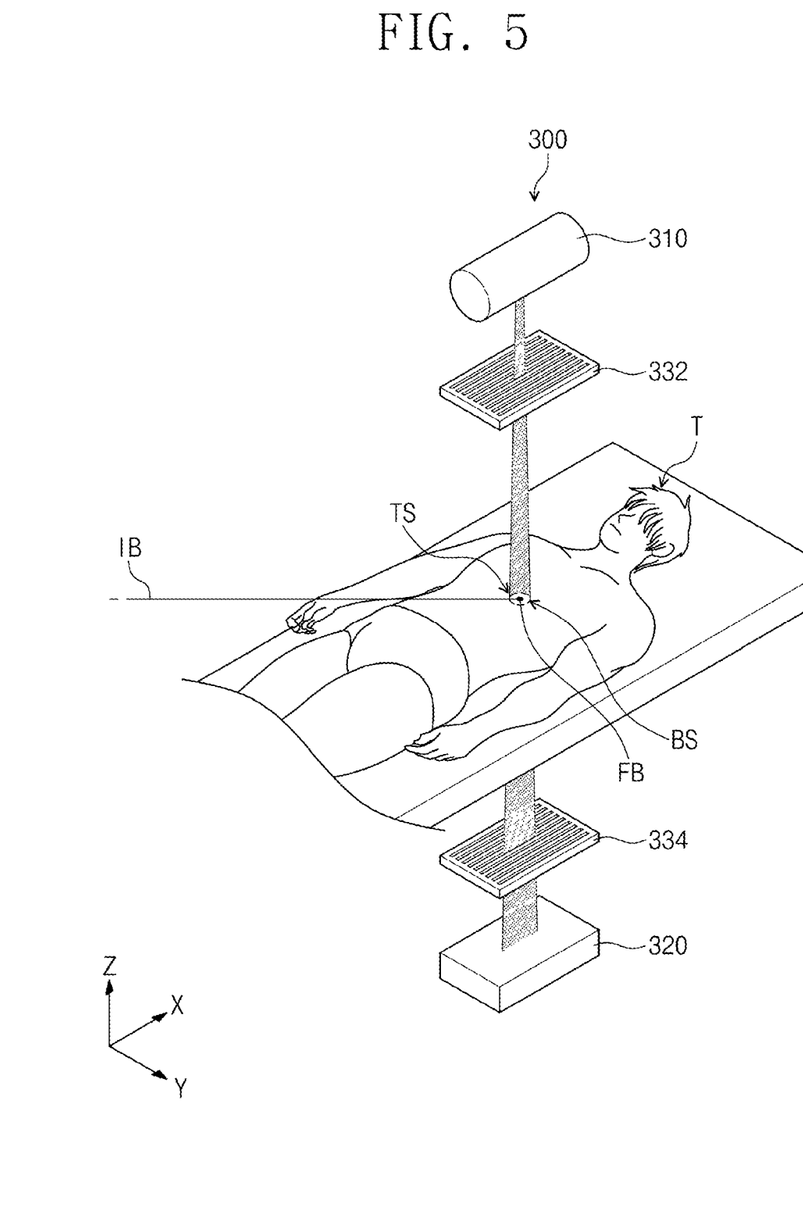
FIG. 5 schematically shows imaging by an X-ray imaging device of FIG. 3.

FIG. 3 schematically shows an ion therapy device 10 according to an embodiment of the inventive concept. FIG. 4 is a drawing of a gantry 200 of FIG. 3 viewed from a front. FIG. 5 schematically shows imaging by an X-ray imaging device 300 of FIG. 3. Hereinafter, referring to FIGS. 3 to 5, the ion therapy device 10 according to an embodiment of the inventive concept will be described. Referring to FIGS. 3 to 5, the ion therapy device 10 may include an ion beam generating unit 110, an ion beam delivering unit 120, an ion beam injecting unit 130, the gantry 200, the X-ray imaging device 300, and a controller 400.

The ion beam generating unit 110 may generate the ion beam IB. The ion beam generating unit 110 may be, for example, a cyclotron or synchrotron. Unlike this, the ion beam generating unit 110 may be a laser acceleration-based generation device, but is not limited thereto. The ion beam IB may be a proton beam or carbon ion beam, but a type of ion is not limited thereto.

The ion beam delivering unit 120 may deliver the ion beam IB generated by the ion beam generating unit 110 to the ion beam injecting unit 130. The ion beam delivering unit 120 may be, for example, a vacuum tube. Although not illustrated, the ion beam delivering unit 120 may further include a magnetic coil provided to enclose the vacuum tube and capable of generating a magnetic field inside the vacuum tube.

The ion beam injecting unit 130 may inject the ion beam IB to a target spot of the body of the examinee T. The ion beam injecting unit 130 may be combined to one side of the gantry 200. For example, the ion beam injecting unit 130 may be combined to an inner side of the gantry 200. The ion beam injecting unit 130 may be combined to the gantry 200 and revolves around the body of the examinee T to inject the ion beam IB to the body of the examinee T at various angles. Although not illustrated, the ion beam injecting unit 130 may include deflection plates for controlling an injection direction of the ion beam IB and adjust energy of the ion beam IB to control an injection depth of the ion beam IB.

The gantry 200 may be provided in a cylindrical type. The gantry 200 may provide an internal space 210 in which the body of the examinee T, the ion beam injecting unit 130, and the X-ray imaging device 300 are provided. The gantry 200 may revolve around the body of the examinee T.

The X-ray imaging device 300 may measure a spot of the microbubble FB formed inside the body of the examinee T. The X-ray imaging device 300 may be at least one of an X-ray phase contrast imaging device, an X-ray subtraction imaging device, and an X-ray tomography imaging device. When the microbubble FB is formed at the Bragg peak spot, the density at the corresponding spot becomes lowered, an X-ray attenuation degree becomes differed, and therefore a phase change in the X-ray penetrating therethrough becomes also differed. In other words, when X-ray images are compared, a difference between the attenuation degrees may occur before and after formation of the microbubble FB at the spot where the microbubble FB is formed. In addition, since the microbubble changes a phase change amount of the X-ray penetrating therethrough, the spot may be figured out where the microbubble FB is formed by analyzing X-ray phase contrast images before and after the formation of the microbubble FB. When large amounts of the microbubble FB are formed, it may be possible to directly check a three-dimensional distribution of the microbubble FB from an X-ray tomography image. Hereinafter, a case where the X-ray imaging device 300 is an X-ray phase contrast imaging device will be exemplarily described.

The X-ray imaging device 300 may include an X-ray generating unit 310, an X-ray detecting unit 320, and first and second gratings 332 and 334. The X-ray generating unit 310 and the first grating 332 are disposed at one side around the body of the examinee T, and the X-ray detecting unit 320 and the second grating 334 may be disposed at the other side around the body of the examinee T. The first and second gratings 332 and 334 may be disposed on the X-ray injection path between the X-ray generating unit 310 and the X-ray detecting unit 320. The first and second gratings 332 and 334 may be disposed to be separated at an identical distance from the body of the examinee T. The X-ray detecting unit 320 may image the spot of the microbubble FB formed inside the body of the examinee T. The X-ray generating unit 310, the X-ray detecting unit 320, and the first and second gratings 332 and 334 may interwork with the gantry 200 to revolve around the body of the examinee T.

The X-ray X injected from the X-ray generating unit 310 and the ion beam IB injected from the ion beam injecting unit 130 may be set to be injected to the target spot TS of the body and the examinee T. At this point, an injection direction of the X-ray X injected to the body of the examinee T and an injection direction of the ion beam IB injected to the body of the examinee T may not overlap each other. In other words, in the gantry 200, except the target spot TS inside the body of the examinee T, the ion beam IB and X-ray X injected into the body of the examinee T may not spatially overlap.

The controller 400 may control the ion beam generating unit 110, the ion beam delivering unit 120, the ion beam injecting unit 130, the gantry 200, and the X-ray imaging device 300. For example, the controller 400 may control an injection time, an injection direction, and an energy intensity, etc., of the ion beam IB and control an X-ray injection time and an injection direction, etc., of the X-ray imaging device 300.

Figure 6:
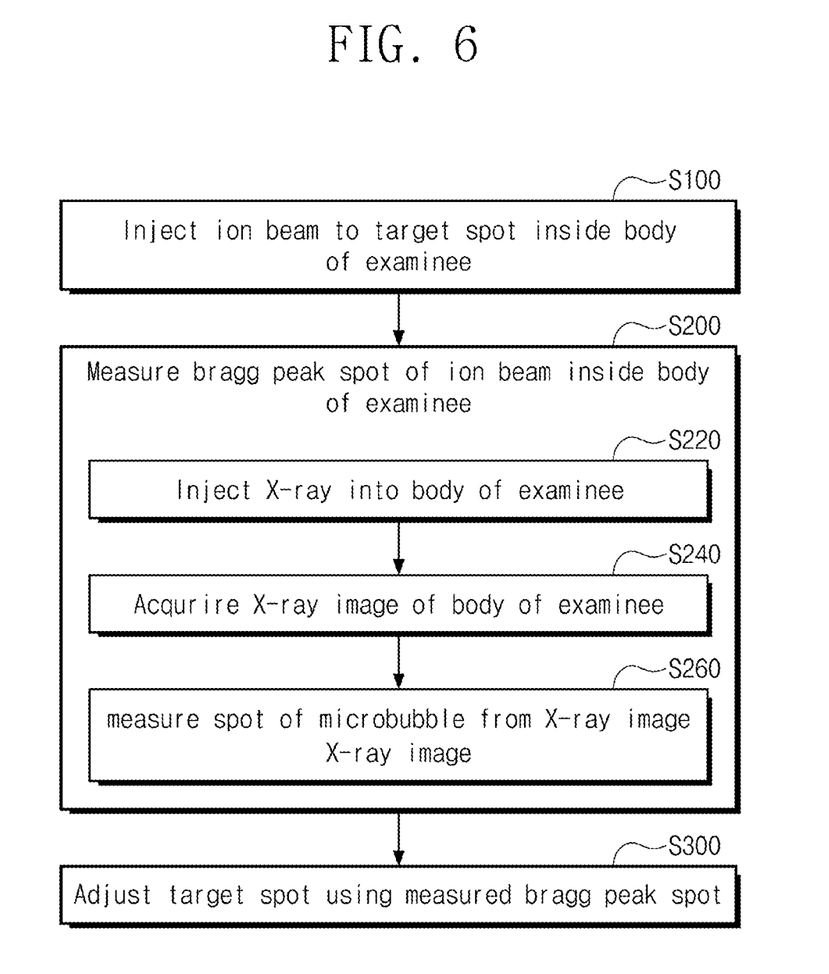
FIG. 6 is a flowchart showing a therapy method for removing a tumor inside the body of an examinee using an ion therapy device of FIG. 3.

FIG. 6 is a flowchart showing a therapy method for removing a tumor inside the body of the examinee T using the ion therapy device 10 of FIG. 3. Hereinafter, a therapy method using the ion beam IB will be described in relation to FIG. 6.

First, the ion beam IB may be injected to the target spot TS inside the body of the examinee T (operation S100). The ion beam IB generated by the ion beam generating unit 110 may be guided to the ion beam injecting unit 130 through the ion beam delivering unit 120 and injected from the ion beam injecting unit 130 to the target spot TS. The ion beam injecting unit 130 may be combined to the gantry 200 to revolve around the body of the examinee T, and inject the ion beam IB at various angles. The ion beam IB may be a proton beam or carbon ion beam, but the type of the ion is not limited thereto.

Then, the controller 400 may measure the Bragg peak spot BS of the ion beam IB inside the body of the examinee T (operation S200). Measuring of the Bragg peak spot BS may include measuring of a spot of the microbubble FB inside the body of the examinee T. As described above, since the microbubble FB is generated at the Bragg peak spot BS, the spot of the microbubble FB may be detected as the Bragg peak spot. The spot of the microbubble FB may be measured using the X-ray imaging device 300.

In detail, the X-ray X may be injected into the body of the examinee T (operation S220). The injection of the X-ray X may be performed substantially at the same time with the injection of the ion beam IB. The X-ray generating unit 310 may interwork with the gantry 200 to revolve around the body of the examinee T, and inject the X-ray X. The injection direction of the X-ray X toward the body of the examinee T and the injection direction of the ion beam IB toward the body of the examinee T may not overlap. An X-ray image of the body of the examinee T may be acquired from the X-ray X (operation S240). The X-ray image may be detected at one of various angles around the body of the examinee T. The X-ray image may be any one of an X-ray phase contrast image, X-ray subtraction image, X-ray phase contrast subtraction image, and X-ray tomography image. From the X-ray image, a spot of the microbubble FB may be measured (operation S260). For example, X-ray images are acquired before and after the ion beam IB is injected into the body of the examinee T, and subtraction is performed on the X-ray images before and after the injection to generate the X-ray subtraction image. In this way, the Bragg peak spot BS at which the microbubble is generated may be directly figured out from the X-ray subtraction image.

The controller 400 may adjust the target spot TS using the measured Bragg peak spot BS (operation S300). For example, the controller 400 may adjust at least one of the injection direction and injection intensity of the ion beam IB to adjust the target spot TS on the basis of the Bragg peak spot BS.

According to the inventive concept, the Bragg peak spot BS of the ion beam IB may be checked by checking the spot at which the microbubble FB is formed inside the body of the examinee T. Accordingly, tumor removal spot information may be obtained along with the tumor removal. In addition, a tumor removal process may be monitored in real time, and a feedback thereabout (e.g. target spot adjustment) may be obtained.

In this specification, it has been exemplarily described that the microbubble is formed at the Bragg peak spot. Unlike this, even though a microbubble may be formed on an injection path of the ion beam, an amount of the generated microbubble is infinitesimal in comparison to an amount generated at the Bragg peak spot. Accordingly, whether the microbubble is generated may function as an indicator for giving information on the Bragg peak spot inside the body of the examinee.

Although the exemplary embodiments of the present invention have been described, it is understood that the present invention may be implemented as other concrete forms without changing the inventive concept or essential features. Therefore, these embodiments as described above are only proposed for illustrative purposes and do not limit the present disclosure.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A therapy method using an ion beam, the therapy method comprising:
   injecting the ion beam to a target spot in a body of an examinee;
   measuring a Bragg peak spot of the ion beam injected into the body of the examinee; and
   adjusting the target spot using the measured Bragg peak spot,
   wherein the measuring of the Bragg peak spot comprises measuring a spot of a microbubble generated inside the body of the examinee.

2. The therapy method of claim 1, wherein the injecting of the ion beam and the measuring of the Bragg peak spot are performed substantially at a same time.

3. The therapy method of claim 1, wherein the adjusting of the target spot comprises adjusting at least one of an injection direction and injection intensity of the ion beam on a basis of the measured Bragg peak spot.

4. The therapy method of claim 1, wherein the measuring of the Bragg peak spot comprises:
   injecting an X-ray into the body of the examinee;
   acquiring, from the X-ray, an X-ray image of the body of the examinee; and
   measuring, from the X-ray image, the spot of the microbubble generated in the ion beam.

5. The therapy method of claim 4, wherein the X-ray image is at least one of an X-ray phase contrast image, X-ray subtraction image, X-ray phase contrast subtraction image, and X-ray tomography image.

6. The therapy method of claim 4, wherein the ion beam and X-ray are injected to the target spot inside the body of the examinee, and an injection direction of the ion beam toward the body of the examinee and an injection direction of the X-ray toward the body of the examinee do not overlap each other.

7. The therapy method of claim 4, wherein the injections of the ion beam and the X-ray are performed during revolution around the body of the examinee.

8. The therapy method of claim 4, wherein a diameter of the microbubble is several hundreds of A to several hundreds of μm.

9. A therapy method using an ion beam, the therapy method comprising:
   injecting the ion beam into a body of an examinee;
   injecting an X-ray into the body of the examinee to which the ion beam is injected;
   acquiring, from the X-ray, an X-ray image of the body of the examinee; and
   measuring, from the X-ray image, a spot of a microbubble generated in the ion beam to check a Bragg peak spot of the ion beam.

10. The therapy method of claim 9, wherein a diameter of the microbubble is several hundreds of A to several hundreds of μm.

11. The therapy method of claim 9, wherein the X-ray image is at least one of an X-ray phase contrast image, X-ray subtraction image, X-ray phase contrast subtraction image, and X-ray tomography image.

12. The therapy method of claim 9, wherein the ion beam and X-ray are injected to a target spot inside the body of the examinee, and an injection direction of the ion beam toward the body of the examinee and an injection direction of the X-ray toward the body of the examinee do not overlap each other.

13. The therapy method of claim 9, wherein the ion beam and X-ray are injected to a target spot inside the body of the examinee,
   further comprising adjusting the target spot using the Bragg peak spot,
   wherein the adjusting of the target spot comprises adjusting at least one of an injection direction and injection intensity of the ion beam on a basis of the measured Bragg peak spot.

14. An ion therapy device comprising:
   an ion beam generating unit configured to generate an ion beam;
   an ion beam injecting unit configured to inject the ion beam to a body of an examinee;
   a gantry disposed to enclose the body of the examinee and configured to revolve around the body of the examinee;
   an X-ray imaging device configured to measure a spot of a microbubble inside the body of the examinee; and
   a controller configured to measure a bragg peak position of the ion beam from the spot of the microbubble.

15. The ion therapy device of claim 14, wherein the X-ray imaging device is at least one of an X-ray phase contrast imaging device, X-ray subtraction imaging device, X-ray phase contrast subtraction imaging device, and X-ray tomography imaging device.

16. The ion therapy device of claim 14, wherein the ion beam injecting unit is combined to one side of the gantry.

17. The ion therapy device of claim 14, wherein the X-ray imaging device comprises non-transitory computer readable instructions which, when executed by a processor, compare images taken before and after the ion beam is injected into the body of the examinee to measure the spot of the microbubble.

* * * * *